United States Patent [19]

D'Alessandro

[11] 4,068,663
[45] Jan. 17, 1978

[54] CONTAINER

[75] Inventor: Alfred C. D'Alessandro, Marblehead, Mass.

[73] Assignee: Aid Pak, Inc., Stoneham, Mass.

[21] Appl. No.: 649,330

[22] Filed: Jan. 15, 1976

Related U.S. Application Data

[63] Continuation of Ser. No. 408,299, Oct. 23, 1973, abandoned.

[51] Int. Cl.² ............................................. A61M 1/00
[52] U.S. Cl. .................................. 128/232; 128/251; 222/541
[58] Field of Search ....................... 222/541, 567, 570; 215/32, 253, 321; 128/251, 232

[56] References Cited

U.S. PATENT DOCUMENTS

| | | | |
|---|---|---|---|
| 2,769,583 | 11/1956 | Darlington | 222/541 |
| 3,187,966 | 6/1965 | Klygis | 222/541 |
| 3,204,799 | 9/1965 | Hunter et al. | 215/321 X |
| 3,589,362 | 6/1971 | Zamarra | 128/251 X |

Primary Examiner—John D. Yasko
Attorney, Agent, or Firm—Wolf, Greenfield & Sacks

[57] ABSTRACT

A fluid dispensing squeeze bottle and nozzle combination in which the bottle is formed of a blow molded resilient plastic with an integrally formed closure having a twist off member that provides an opening in the cover when twisted. The cover is also formed with a cantilevered top having a tapered wall. The cover and top snap-fit into a corresponding recess within one end of a separate nozzle. The nozzle recess is provided with an annular flange adapted to engage the cantilevered top of the bottle cover to form a fluid impervious seal.

11 Claims, 3 Drawing Figures

CONTAINER

This is a continuation, of application Ser. No. 408,299, filed Oct. 23, 1973 now abandoned.

FIELD OF THE INVENTION

The present invention relates to a single-use disposable squeeze bottle and nozzle, particularly adapted for use as a disposable douch and, with an appropriate nozzle, an enema.

BACKGROUND OF INVENTION

Heretofore commercially available douches have been manufactured of a series of interlocking components including a fluid containing bottle, a cover for the bottle, an interlocking mechanism for attaching a nozzle, and a nozzle to be secured to the bottle when the cover is removed. In some commercially available douches additional elements are also included such as a valve for controlling the amount of fluid flow from the open neck bottle into the nozzle. These units which are widely used are generally made of injection molded plastic and are sold in kits for assembly prior to use. Such units are relatively expensive because of the number of components involved. These components must be separately molded and assembled with the attendant dye molding and assembly costs. In addition these and other related units must be carefully assembled by the user in order to avoid inadvertent leakage which will occur if the nozzle is not securely screwed by the collar to the bottle. Such leakage can readily occur as a result of careless assembly or loosening during use.

In addition, in certain douche and syringe type applications, it is important to maintain clean or sterile conditions in the fluid being dispensed from the bottle. Such sterile conditions are not as easily maintained during manufacture or subsequent usage when the bottle has to be opened to insert the fluid and thereafter when the bottle is frequently opened to attach the nozzle.

OBJECTS OF THE INVENTION

It is an object of the present invention to overcome the deficiencies of the prior art devices as described above.

Thus it is an object of the present invention to provide an improved syringe-like dispenser which is adapted to be formed in a blow-molding technique wherein the fluid content of the bottle intended to be dispensed is placed in the bottle as it is being assembled under conditions in which sterility or cleanliness of the fluid may be more readily maintained.

It is also an object of the present invention to provide a squeeze bottle having a clean or sterile fluid in which the blow-molded bottle is so designed as to provide a cover which may readily be opened by a twist-off key or the like.

A further object of the present invention is to provide a fluid containing blow molded bottle having an integrally formed cover that snaps into a mating recess in a nozzle.

A further object of the present invention is to provide an improved blow-molded squeeze bottle design for use as a fluid dispensing media in conjunction with an interlocking nozzle in which the locking mechanism between the cover of the bottle and the mating recess in the nozzle is provided with a self sealing gasket like seal.

A still further object of the present invention is to provide an improved sealing means for a bottle and nozzle of the type herein described, wherein an annular sealing ring integrally formed with the nozzle is pressured into a more effective fluid seal by the exertion of pressure on the bottle when the bottle is in use.

A still further object of the present invention is to provide an improved sealing means for a bottle and nozzle of the type herein described in which a cantilevered cover maintained in normal tension relation with an annular gasket-like ring at the nozzle cover interface provides a fluid impervious seal.

One further object of the present invention is to provide an improved interlock for securing a nozzle to the cover of a blow molded bottle in such a manner as to effect an improved seal therebetween.

SUMMARY OF THE INVENTION

To accomplish the foregoing and other objects of this invention there is provided a fluid containing squeeze bottle having an integrally formed twist-open cover, a nozzle attachment having a recess adapted to receive the twist-open cover, and means for engaging the cover so as to lock the nozzle to the bottle and provide a fluid impervious seal.

In the preferred embodiment the twist-open cover is formed with a cantilevered dome-like structure and key, the key being easily grasped and twisted so as to fracture the thin plastic wall at the top of the dome, thereby creating an opening at the top of the bottle. The nozzle is formed with a basically cylindrical recess that closely contacts the cover. The side wall of the recess is formed with a U-shaped annular cutout that engages a similar shaped shoulder on the cover, while the closed end of the recess is hemispherically shaped and formed with a donut-shaped annular gasket that extends from the recess and makes contact with the cantilevered dome-like top of the cover. When the bottle is squeezed the increased pressure from the contained liquid due to the decreased volume deforms the cantilevered top around the annular gasket thereby improving the seal between bottle and nozzle.

BRIEF DESCRIPTION OF THE DRAWINGS

The foregoing objects and advantages of the present invention will be more clearly understood when considered in conjunction with the accompanying drawings, in which.

DETAILED DESCRIPTION OF THE DRAWINGS

Figures 1, 2, 3:
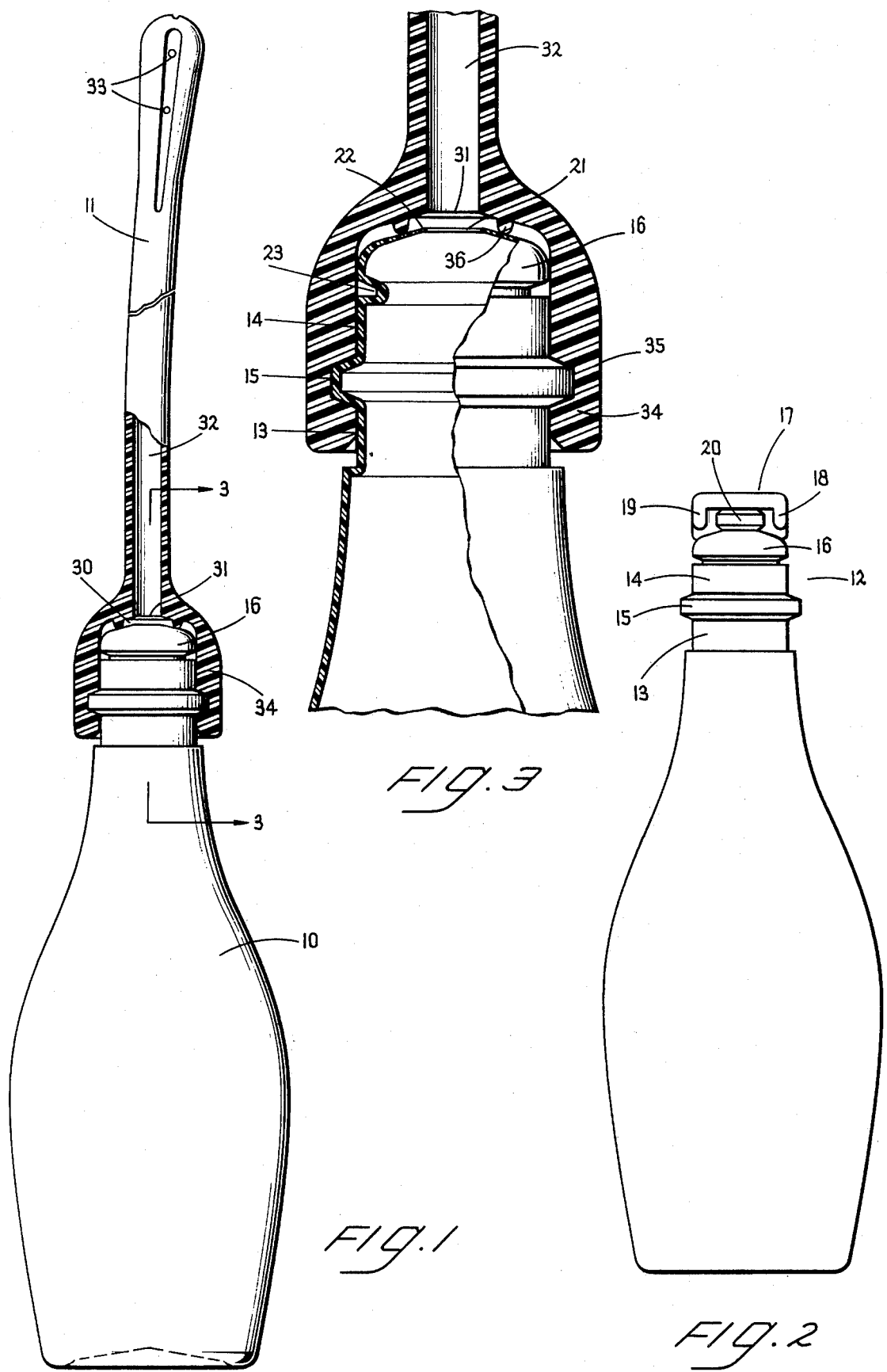
FIG. 1 is an elevational view of a bottle and nozzle combination showing the bottle with the twist-off closure removed and the bottle and nozzle ready for use.
FIG. 2 is a fragmentary view of a top of a bottle with a twist-off member in place.
FIG. 3 is a cross sectional detail taken along the line 3—3 of FIG. 1.

As illustrated in FIG. 1 there is shown a bottle 10 and a nozzle 11. The bottle 10 is made in known blow-molding equipment from elongated tubes of thermoplastic material in a process in which the fluid content of the bottle is injected into the elongated thermplastic tube at the same time as the tube is being shaped by a die into the bottle configuration. By utilizing this technique, sterile or clean fluid, such as water, antiseptics or the like may be simultaneously contained within the bottle as the bottle is being formed, thus avoiding unnecessary contamination or exposure to contamination of the bottle or its contents.

In this blow-molding technique, the cap or cover of the bottle is simultaneously formed and sealed. This eliminates the need of making and attaching a separate cover. The bottle and cover may be formed of a wide variety of materials such as low and high density polyethylene, polypropylene or polystyrol. Similarly the fluid content of the bottle may also comprise a wide variety of materials, such as water, antiseptics, fluid soaps, etc.

The bottle is made with a wall thickness that may vary as hereinafter described, and a general overall thickness that depends in large measure upon the specific applications and and size of the bottle. In general, thickness should be such as to permit the bottle to be hand squeezed for ejection of the fluid through the nozzle. Thus, for example, a bottle containing 3 to 6 ounces of water may have a wall thickness, the order of magnitude of which is, between 0.03 and 0.07 inches when the bottle is made of low density polyethylene.

Referring now to FIGS. 2 and 3 where there is illustrated the cover 12 of the bottle 10, it will be noted that cover 12 is formed with a relatively thick-walled, two-part throat section 13 and 14, separated by an annular shoulder 15. Shoulder 15 is formed with symmetrical sloping sides on the top and bottom, the slope being approximately 25° from the horizontal and serves as a means for securing nozzle 11 as hereinafter described. Throat section 14 is terminated by an orthogonal wall that forms dome support 23.

The top of the cover 16 has a dome-like configuration. As illustrated in FIG. 3 dome 16 tapers from a comparatively thick wall at its base, dome support 23, to a relatively thin wall at 22 surrounding bottle opening 21. Because of this tapered construction and the cantilivered support provided at wall 23, the top surface of dome 16 is easily deformed.

In addition, since the wall at 22 surrounding bottle opening 21 is thin, it is adapted to be fractured or severed when the twist-off key or element 17 is turned sharply. The twist-off key or element 17 is provided with bulb-like portion 20 and extending arm 18 and 19 which are adapted to facilitate grasping and provide leverage for twisting the element off. When arms 18 and 19 are twisted, bulb 20 severs from dome 16 at wall section 20.

The nozzle 11 is of conventional outer configuration and is provided with a recess 30 that is intended to mate with cover 12. The closed end of recess 30 includes opening 31 that leads into passageway 32. Passageway 32 travels the length of nozzle 11 and terminates with portals 33. When bottle 10 is squeezed the decrease in volume forces the contained liquid through opening 21 in the bottle and opening 31 in the nozzle up passageway 32 and out portals 33.

Recess 30 also includes means for securing nozzle 11 to bottle cover 12. Side-wall 34 is formed so as to closely contact cover 12 thereby giving recess 30 a basically cylindrical shape. In particular side-wall 34 includes V-shaped annular cut-out 35 adapted to receive shoulder 15 and donut shaped ring 36, an integrally formed annular protrusion extending down from the top of recess 30 and concentric to nozzle opening 31. When nozzle 11 is snapped onto cover 12, cut-out 35 engages shoulder 15 while ring 36 is pressured into contact with dome 16.

To use the douche apparatus herein described the user first turns the twist-off key or element 17 until it is free of the bottle cover 12. The nozzle 11 is then pressed on to the cover 12 until shoulder 15 engages cut-out 35. In this arrangement the cantilevered dome 16 engages the annular ring 36 under slight tension. This integral arrangement thus provides a tight seal when the nozzle 11 is secured to the open bottle 10. When the bottle 10 is squeezed to eject the fluid through bottle opening 21 and into the nozzle opening 31, the pressure of the hand-squeeze verti-flexes or presses the cantilever dome 16 into increased pressure engagement with the annular ring 36 thereby improving the effectiveness of the seal when the unit is in use.

Having described the preferred embodiment, it should now be apparent to one skilled in the art that numerous other embodiments and modifications thereof may be constructed, all of which are contemplated as falling within the spirit and scope of this invention.

What is claimed is:

1. In combination, a Fluid containing plastic squeeze bottle having an integrally formed cover, a nozzle attachment having an integrally formed means for removably interlocking said nozzle to said cover, said cover having a dome with an opening formed therein by twisting off an integral twist off member along an annularly shaped thin section in said dome, said dome comprising a cantilever section and an integral annular depending skirt about its outer periphery, said opening being formed in the center of said cantilever section and defined solely by the thickness of said thin section, said skirt having a thickness greater than the thickness of said cantilever section whereby said cantilever section may be deflected in the direction of the axis of said skirt, said nozzle attachment having means defining a downwardly depending internal annular ring engaging said cantilever section in a fluid tight seal about the periphery of said opening and a passage extending through the nozzle attachment terminating at one end in a plurality of portals and at the other end in an opening with the annular ring disposed adjacent to and concentric with the opening in the nozzle attachment, the openings in the nozzle attachment and dome being of comparable size and the cantilever section extending a sufficient distance to define the opening in the dome.

2. A combination as set forth in claim 1 wherein said cover also includes a throat section and annular dome support section both of which are integrally formed with the dome, the throat section being at least partially of cylindrical shape and the dome support section formed by an annular inwardly directed channel coupled intermediate the top of the throat section and the skirt.

3. A combination as set forth in claim 2 wherein said throat section includes separate throats separated by an annular shoulder, said nozzle having an annular cut-out for mating with the annular shoulder to secure the nozzle on the bottle with the annular ring of the nozzle tending to deflect the cantilever section when the nozzle is in place.

4. A combination as set forth in claim 3 wherein the cantilever section is tapered from the skirt to its inner free end.

5. A combination as set forth in claim 1 wherein said opening is defined solely by an edge of the cantilever section and wherein opposite points on the edge are in facing relationship.

6. A disposable douche product comprising:
a flexible container having a body and a head at one end thereof at least a portion of which has a greater radial rigidity than the body, the head including a neck extending from the container, an annular collar integrally formed on the neck and spced from the container, the collar having opposed sloped shoulders forming a tapered collar, a first passageway through said head, a plug integrally formed on the exterior surface of the end of said head distal from the container and obturating said passageway, said plug having a weakened section to facilitate severing said plug from said head and opening said passageway;

a douching liquid sealed within said container, the quanitity of said liquid being that needed for a single application; and a pipe adapted to be sealingly snap-fitted onto the exterior surface of said head after said plug is severed from said head, said pipe including an annular skirt base portion defining a cavity therein and an annular recess spaced from the proximate end of the base, the proximate base end being the end adapted to be closest to the container when the pipe is mounted on the container head, the recess being formed in the interior surface of the skirt and conforming to the mating shape of said collar, an elongated flexible nozzle section having a second passageway therethrough communicating with said cavity, a plurality of apertures through the distal end of said nozzle section communicating with said second passageway, said first and second passageways being in flow communication when said plug is severed from said head and said pipe is mounted on said head whereby squeezing said container effects ejecting said douching liquid through said apertures.

7. A disposable douche product as defined in claim 6 wherein said proximate end of the base is beveled from the interior surface of the skirt toward the exterior surface to facilitate snap fitting the pipe onto the container head.

8. A disposable douche product as defined in claim 6 wherein the distal end of said pipe is formed with at least one recessed section and wherein said apertures extend through said recessed section.

9. A disposable douche product as defined in claim 8 wherein the distal end of said pipe has a general cruciform configuration.

10. A disposable douche product comprising;

a container including a flexible, blow-molded, plastic, elongated container body and a head at one end thereof, the head including a neck extending from one end of the container body, an annular collar integrally formed on the exterior surface of the neck and spaced from the container, the collar having spaced apart opposed sloped annular shoulder forming a tapered collar, the collar and the portions of the neck contiguous to the collar having a greater radial rigidity than said body, a first passageway through said head, a plug integrally formed on the exterior surface of the end of said head distal from the container body and obturating said first passageway, said plug having a weakened section and a projection extending transversely therefrom to facilitate manually grasping said plug to effect severing of said plug from said head at said weakened section and opening said passageway;

a douching liquid sealed within said container, the quantity of liquid being that needed for a single application; and a pipe adapted to be sealingly snap-fitted onto the exterior surface of said head after said plug is severed from said head, said pipe including an annular skirt base defining a cavity therein, an annular recess spaced from the proximate end of the base, the proximate base end being the end adapted to be closest to the container body when the pipe is mounted on the head, the recess being formed in the interior surface of the skirt and conforming to the dimensions and shape of said collar, the proximate end of the base being beveled from the interior surface thereof toward the exterior surface to facilitate snap fitting the pipe onto the container head, an elongated flexible nozzle section having a second passageway therethrough and communicating with said cavity, a plurality of apertures through the distal end of said nozzle section communicating with said second passageway, said first and second passageways being in flow communication when said plug is severed from said head and said pipe is snapped onto said head so that squeezing said container effects ejecting said liquid through said pipe and out through said apertures.

11. A disposable douche product as defined in claim 10 wherein the distal end of said pipe is formed with a plurality of recessed sections and wherein said apertures extend through said recessed sections.

* * * * *